(12) United States Patent
Ahrens et al.

(10) Patent No.: US 9,987,412 B2
(45) Date of Patent: Jun. 5, 2018

(54) ATTACHMENT ASSEMBLY FOR ATTACHING A FLUID BAG TO A FLUID WARMER OF A SYSTEM FOR EXTRACORPOREAL BLOOD TREATMENT

(71) Applicant: B. BRAUN AVITUM AG, Melsungen (DE)

(72) Inventors: Joern Ahrens, Baunatal (DE); Máté Bocz, Budapest (HU); Jean-Paul Menneguerre, Pully (CH)

(73) Assignee: B. BRAUN AVITUM AG, Melsungen (DE)

( * ) Notice: Subject to any disclaimer, the term of this patent is extended or adjusted under 35 U.S.C. 154(b) by 309 days.

(21) Appl. No.: 14/887,974

(22) Filed: Oct. 20, 2015

(65) Prior Publication Data
US 2016/0121038 A1    May 5, 2016

(30) Foreign Application Priority Data
Nov. 3, 2014 (EP) ..................... 14191432

(51) Int. Cl.
*A61M 37/00* (2006.01)
*A61M 1/36* (2006.01)
(Continued)

(52) U.S. Cl.
CPC ............... *A61M 1/369* (2013.01); *A61J 1/10* (2013.01); *A61J 1/1462* (2013.01); *A61J 1/16* (2013.01);
(Continued)

(58) Field of Classification Search
CPC .... A61M 1/369; A61M 1/1638; A61M 1/166; A61M 1/1668; A61M 1/3601;
(Continued)

(56) References Cited

U.S. PATENT DOCUMENTS 3,656,873 A      4/1972   Schiff
2003/0220598 A1*  11/2003  Busby .................... A61M 1/28
                                                        604/5.01
(Continued)

FOREIGN PATENT DOCUMENTS

CN      104958796 A    10/2015
CN      205649682 U    10/2016
(Continued)

OTHER PUBLICATIONS

European Search Report for EP 14191432.5 dated Mar. 31, 2015.
(Continued)

*Primary Examiner* — Philip R Wiest
(74) *Attorney, Agent, or Firm* — RatnerPrestia

(57) ABSTRACT

An attachment assembly for attaching a fluid container to a fluid warmer of a system for extracorporeal blood treatment is disclosed. The assembly includes a hook-shaped fixture located on the fluid warmer, a pin-shaped fixture located on the fluid warmer, and receiving members located on the fluid container to receive the hook-shaped fixture and the pin shaped fixture located on the fluid warmer. A fluid warmer containing a hook-shaped fixture located on the fluid warmer and a pin-shaped fixture located on the fluid warmer of a fluid bag attachment assembly is also disclosed. Tubing guides present on the fluid warmer in conjunction with tubes of differing lengths attached to the fluid bag reduce the occurrence of usage errors during insertion of the fluid bag into the fluid warmer.

11 Claims, 2 Drawing Sheets

(51) Int. Cl.
*A61M 39/12* (2006.01)
*A61J 1/10* (2006.01)
*A61M 1/28* (2006.01)
*A61J 1/14* (2006.01)
*A61J 1/16* (2006.01)
*A61M 1/16* (2006.01)

(52) U.S. Cl.
CPC .......... *A61M 1/166* (2014.02); *A61M 1/1629* (2014.02); *A61M 1/1668* (2014.02); *A61M 1/28* (2013.01); *A61M 1/3601* (2014.02); *A61M 39/12* (2013.01); *A61M 2205/36* (2013.01)

(58) Field of Classification Search
CPC .... A61M 1/28; A61M 39/12; A61M 2205/36; A61J 1/10; A61J 1/1462; A61J 1/146
USPC ................. 604/4.01–6.16, 403–416
See application file for complete search history.

(56) References Cited

U.S. PATENT DOCUMENTS

2009/0105629 A1   4/2009   Grant et al.
2012/0152118 A1   6/2012   Weaver et al.

FOREIGN PATENT DOCUMENTS

| JP | 2009191690 A | 7/2002 |
| JP | 2005192784 A | 7/2005 |
| WO | WO 2006/120415 | 11/2006 |
| WO | WO 2011/112317 | 9/2011 |

OTHER PUBLICATIONS

Japanese Notification of Reasons for Rejection with English language translation for Application No. 2015-191778, dated Jun. 30, 2017, 14 pages.
Chinese Office Action for Chinese Application No. 201510660845.8, dated Jan. 17, 2018, including English translation, 11 pages.

* cited by examiner

ATTACHMENT ASSEMBLY FOR ATTACHING A FLUID BAG TO A FLUID WARMER OF A SYSTEM FOR EXTRACORPOREAL BLOOD TREATMENT

CROSS REFERENCE TO RELATED APPLICATIONS

This application claims priority to European application EP 14191432.5 filed Nov. 3, 2014, the contents of such application being incorporated by reference herein.

FIELD OF THE INVENTION

The present invention relates to an attachment assembly for attaching a fluid bag to a fluid warmer of a system for extracorporeal blood treatment, as well as a fluid warmer and a fluid container.

BACKGROUND OF THE INVENTION

A very frequent issue faced during extracorporeal blood treatment (e.g., haemodialysis) is the occurrence of hypothermia episodes due to the level of fluid exchange and/or cool fluids coming into contact with the bodily fluids of a patient. Thus, many systems for extracorporeal blood treatment comprise an integrated fluid warmer used to warm up fluids before they are used for haemodialysis, thereby helping the patient to continuously maintain a stable body temperature.

Such fluid warmers usually have an interface with a disposable container (e.g., a bag) of fluid, where heat is transferred from the fluid warmer to the fluid flowing in the disposable container. To ensure adequate heat transfer, it is necessary that the contact interface between the fluid warmer and the disposable container has a large surface area and the disposable container lies flush against the surface of the fluid warmer. Hence, proper insertion/attachment of the disposable container into/to the fluid warmer is paramount to ensuring a good interface and thus efficient heat transfer between fluid warmer and fluid container.

However, during the hectic daily clinical routine, it easily happens that disposable containers are attached to a fluid warmer in a wrong way. Especially when fluid bags instead of hard-shelled fluid containers are used to contain the fluid to be warmed, folding of an incorrectly attached fluid bag can obstruct fluid flow through the fluid bag. Furthermore, the occlusion of inlet and outlet tubes connecting the fluid bag to the heamodialysis machine can disrupt fluid flow or can cause potentially dangerous air bubbles to remain in the tubes. Hence, proper attachment of the fluid bag to the fluid warmer is essential to protect a patient from hypothermia and/or air bubbles and thus to ensure patient safety during extracorporeal blood treatment. In contrast to hardshelled fluid containers, fluid bags offer the advantage of a cheaper alternative while also producing a smaller waste volume after use. Hence, many hospitals rely heavily on the use of fluid bags instead of hard-shelled containers. Due to the inherent structural instability of fluid bags, the above mentioned problems of obstruction of fluid flow/occurrence of air bubbles may arise due to usage error during the insertion of such fluid bags into fluid warmers. Hence relatively experienced clinical personnel is required for the insertion of fluid bags into fluid warmers to ensure patient safety. This ultimately increases the cost of extracorporeal blood treatment.

DESCRIPTION OF THE RELATED ART

To address the issue of air bubbles in the extracorporeal circuitry, prior art documents US 20120152118 and WO2011/112317 disclose several venting devices arranged at the extracorporeal circuitry of a haemodialysis machine.

Document US 20120152118 discloses a gas release device including an elongate vertical portion and a flared portion extending outwardly from the vertical elongate portion. Furthermore, the device includes an inlet port for delivering a bodily fluid into the device, and an outlet port for evacuating bodily fluid from the device. The inlet port is positioned below the elongate vertical portion and the outlet port is positioned below the flared portion so that bodily fluid travelling from the inlet port towards the outlet port is forced around the flared portion, thereby causing air bubbles in the bodily liquid to be recirculated back towards the inlet port.

Document WO2011/112317 describes a venting device for a dialysis system including a fluid inlet line, a venting device in fluid communication with the fluid inlet line, and a fluid outlet line in fluid communication with the venting device. The venting device can include a housing defining a fluid chamber, a valve member disposed above the fluid chamber between a lower seat and an upper seat and a pump operable to draw fluid into the fluid chamber from the fluid inlet line and to force fluid out of the fluid chamber and into the fluid outlet line.

These two documents emphasise the need to remove air bubbles from fluid lines. However, neither of these documents suggests addressing the cause of the occurrence of these air bubbles (e.g., due to aberrant fluid bag loading in to a fluid warmer) to prevent the occurrence of air bubbles in the first place.

Document US200825347A1 discloses the use of sensors to monitor whether fluid contained in a disposable container or cassette is properly warmed. To this end, the cassette includes a thermal well to permit the sensing of various properties of the fluid. This thermal well includes a hollow housing made of a thermally conductive material. In other embodiments the cassette includes sensor leads in order to sense various properties of the fluid. The thermal well has an inner surface shaped so as to form a mating relationship with a sensing probe. Thus, the inner surface of the thermal well is thermally coupled to the sensing probe. In some embodiments, the thermal well is located on a disposable portion and the sensing probe is located on a reusable portion of the cassette.

Similarly, document WO2006/120415 discloses the use of sensors to monitor the operation of a fluid container, in this case a cartridge.

Due to the need of sensors, the temperature monitoring strategy disclosed in document US200825347A1 is rather expensive. Furthermore, the mating relationship between the sensing probe and the thermal well unnecessarily overcomplicates the insertion procedure of the cassette.

The topic of facilitating easy attachment of several components of a dialysis machine to each other, has been addressed with respect to a blood circuit assembly that can be attached to a dialysis unit via engaging locks and connectors. Such a system is disclosed e.g., in document US20090105629A1. However, this document does not address the topic of properly attaching a fluid bag to a fluid warmer in order to ensure accurate fluid warming, while also reducing the occurrence of air bubbles.

Other known methods of attaching a fluid container to a fluid warmer of a heamodialysis system include complicated attachment assemblies e.g., including six metal pins required to position the fluid bag in the fluid warmer and to hold it in place. Often, some of these pins are rather difficult to reach, especially by a nurse carrying a heavy fluid bag. This increases the susceptibility of the attachment assemblies to usage error. Furthermore, such complicated attachment assemblies are expensive to manufacture and hence unnecessarily increase the cost of heamodialysis.

SUMMARY OF THE INVENTION

It is an object of the present invention to provide a simple and cheap attachment assembly, a fluid warmer and a fluid container allowing the easy attachment of a fluid container to a fluid warmer in only the one desired way, thereby ensuring efficient heat transfer between the fluid warmer and the fluid to be warmed, and reducing the probability of usage error during attachment of the fluid container to the fluid warmer.

This object is achieved by the attachment assembly of the independent claim, the claimed fluid warmer, the claimed fluid container and the claimed system for extracorporeal treatment of patient' fluid. Advantageous modifications are the subject of the sub claims.

The gist of the invention lies in providing an asymmetric attachment assembly with a number of fixtures, preferably L-shaped hooks mounted onto a fluid warmer on which a fluid bag having corresponding openings can be hung and a number of pins or knobs mounted onto the fluid warmer used to fix the fluid bag hung onto the hooks in position. The hooks allow an easy and weight-bearing attachment of a fluid bag to a fluid warmer. Once the fluid bag hangs on the hooks, the bag needs to be stretched a little to engage with the pins/knobs. This ensures a tight/flush fit between the fluid bag and the heat exchange surface of the fluid warmer, thus preventing folding of the bag or accidental occlusion of tubes connected to the bag and allowing for efficient fluid flow and heat transfer at the interface between the fluid warmer and the fluid contained within the fluid bag. To ensure that the fluid bag can only be attached to the fluid warmer in the one desired orientation and/or position, the fluid warmer comprises guiding means for the inlet and outlet tubes attached to the fluid bag. These guiding means are recesses/grooves which define a predetermined path for the inlet and outlet tubes of the fluid bag each. The paths defined by the guiding means for the inlet and outlet tubes of the fluid bag are of different lengths, as are the lengths of the inlet and outlet tubes. Thus, only if the fluid bag is correctly attached to the fluid warmer (and thus the long tube runs along the long path and the short tube runs along the short path) it is possible to fluidly connect the fluid bag to the haemodialysis machine using the inlet and outlet tubes attached to the fluid bag. Thus, the attachment of a fluid bag to the fluid warmer is facilitated, malfunction of the haemodialysis system due to user error is reduced and optimal heat transfer at the interface between the fluid warmer and the fluid bag is ensured.

An attachment assembly according to aspects of the present invention for attaching a fluid container such as a fluid bag to a fluid warmer of a system for extracorporeal blood treatment, comprises
  at least one hook-shaped fixture located on the fluid warmer,
  at least one pin-shaped fixture located on the fluid warmer, and
  at least two receiving members located on the fluid container to receive the at least one hook-shaped fixture and the at least one pin shaped fixture located on the fluid warmer.

This attachment assembly is simple and cheap to manufacture and allows for an easy attachment of the fluid bag to the fluid warmer.

To ensure an easy and weight-bearing initial attachment of a fluid bag to the fluid warmer, the at least one hook-shaped fixture is located and arranged on the fluid warmer in such a way, that a fluid bag can be hung on the at least one hook-shaped fixture, i.e. the at least one hook-shaped fixture opens in upward or sideward direction when viewed by a use/nurse attempting to attach the fluid bag to the fluid warmer. When hanging the fluid bag onto the at least one hook-shaped fixture, the least one hook-shaped fixture is inserted into a corresponding receiving member e.g., an opening in the fluid bag or a strap, flap, tab or something similar located on the fluid bag and configured to receive the at least one hook-shaped fixture. The fact that the weight of the fluid bag is supported by the at least one hook-shaped fixture located on the fluid warmer, renders the attachment assembly considerably more user-friendly, as the nurse's hand becomes free as the bag is hung on the first hook i.e. until the at least one hook-shaped fixture is inserted into the corresponding receiving member of the fluid bag and the nurse can use both hands to attach the remaining 3 corners. The bag can then subsequently be fixed into position. During this positioning step, the nurse does not have to bear the weight of the fluid bag, which greatly facilitates accurate positioning of the fluid bag, as the nurse is not distracted by the bodily effort of carrying heavy loads.

To fixate the fluid bag in the desired position, in which the fluid bag is stretched to its full length and fits flush against the fluid warmer, at least one pin-shaped fixture is provided on the fluid warmer. This pin-shaped fixture is located and arranged on the fluid warmer at a distance from the at least one hook-shaped fixture. This distance is dimensioned in such a way, that when a fluid bag is attached to the at least one hook-shape fixture and stretched to its full length, the at least one pin-shaped fixture can be inserted into a corresponding receiving member e.g., an opening in the fluid bag or a strap, flap, tab or something similar located on the fluid bag and configured to receive the at least one pin-shaped fixture.

In other words, the fluid container attachment assembly of the system for extracorporeal blood treatment (dialyses machine) according to aspects of the present invention comprises the one (first) fixture, for example a hook, located on/at the fluid warmer of the system which first fixture is adapted to carry the flexible fluid container at its one (first) receiving member, for example a through hole or loop, of the container and the other (second) fixture, for example a pin or knob, also located on/at the fluid warmer which second fixture is adapted to stretch the already carried flexible fluid container along the warmer (along a surface of the warmer) by engaging the other (second) receiving member, for example a through hole or loop, of the container. Accordingly, the distance between the first and second fixture is preferably greater than the distance of the first and second receiving member. Furthermore, the first and second fixture are preferably distanced in vertical direction wherein the first fixture is located above the second fixture.

In an advantageous embodiment of the present invention, the at least one pin-shaped fixture is an essentially arrow-shaped pin/knob/projection present on the surface of the fluid warmer. Similarly to an arrow, the at least one pin-shaped fixture comprises a cylindrical shaft onto which a conical tip is mounted at the end of the shaft projecting outwardly from the surface of the fluid warmer. The base diameter of the cone constituting the tip of the arrow is larger than the diameter of the shaft. Thus, the at least one pin-shaped fixture can be inserted into the receiving opening of a fluid bag, until the shaft of the at least one pin-shaped fixture projects through the receiving opening. In this position, the increased diameter of the conical tip of the at least one pin-shaped fixture prevents any undesired retraction of the at least one pin-shaped fixture against the insertion direction. Hence, the fluid bag is securely locked into position, until a user/nurse removes the fluid bag from the at least one pin-shaped fixture again by actively pulling the fluid bag of the pin-shaped fixture.

To ensure optimal heat transfer between the fluid warmer and the fluid bag, the fluid bag has to be stretched to its full length and needs to lie flat against the surface of the fluid warmer. Thus, in an advantageous embodiment of the present invention, the distance between the at least one hook-shaped fixture located on the fluid warmer and the at least one pin-shaped fixture located on the fluid warmer is adapted in its dimension to ensure that a fluid bag attached to the at least one hook-shaped fixture located on the fluid warmer at one end and attached to the at least one pin-shaped fixture located on the fluid warmer at another end lies flush against the fluid warmer. This generally means that the at least one hook-shaped fixture and the at least one pin-shaped fixture are located on the fluid warmer essentially adjacent to the area of the heat transfer interface between fluid bag and fluid warmer.

In an advantageous embodiment of the present invention, the at least one hook-shaped fixture located on the fluid warmer and the at least one pin-shaped fixture located on the fluid warmer are manufactured out of a polymer material. In contrast to metal, polymer material reduces the risk of an accidental rupturing of a fluid bag or container on these fixtures. However, preferentially this polymer material must provide the necessary structural strength and durability to bear the weight of a fluid bag or container during the attachment of the fluid container to the fluid warmer.

Another aspect of the present invention concerns a fluid warmer with at least one hook-shaped fixture located on the fluid warmer and at least one pin-shaped fixture located on the fluid warmer of a fluid bag attachment assembly as discussed above.

Such a fluid warmer advantageously comprises a rear housing part and a front housing part connected to each other via hinges. For example, the rear housing part can take the form of a door that can be opened by a user/nurse to insert a fluid bag into the fluid warmer. After the door has been opened and the fluid bag has been attached to the front housing part, the door is closed again and the fluid bag comes to lie between the front and rear housing parts, thereby being pressed flat against a keramic heat exchange surface of the first housing part of the fluid warmer. To facilitate the insertion of a fluid bag into such a fluid warmer, the at least one hook-shaped fixture located on the fluid warmer is located preferably next to the heat exchange interface of the fluid warmer next to the hinge area. The hinge area is generally harder to reach for a user/nurse, hence arranging the at least one hook-shaped fixture in this area improves the ease of fluid bag insertion into the fluid warmer, as the receiving member, e.g., the opening of the fluid bag can simply be pulled over the hook-shaped fixture without much inconvenience. The at least one pin-shaped fixture located on the fluid warmer is preferably located on the other side of the heat exchange interface of the fluid-warmer opposite of the side where the at least one hook-shaped fixture is located. Thus, the fluid bag can be easily inserted using the least one hook-shaped fixture located in the hard-to-reach hinge area and subsequently fixed into position using the at least one pin-shaped fixture located in a more accessible area.

In an advantageous embodiment of the invention, the at least one hook-shaped fixture and the at least one pin-shaped fixture are arranged immediately adjacent to the area of an interface between the fluid warmer and a fluid bag attached to the fluid warmer. This ensures that the fluid bag is stretched to its full length (e.g., no obstruction of fluid flow due to folding of the fluid bag) and fits flush against the heat exchange interface.

To ensure the fluid container/bag can be inserted in only the one desired way and tubes such as inlet and outlet tubes attached to the fluid bag are connected correctly before heamodialysis is commenced, the fluid warmer preferably comprises guiding means for tubes connected to a fluid bag attached to the fluid warmer, which indicate the correct position of each tube. These guiding means preferentially take the form of recesses or grooves in the housing of the fluid warmer, but also can be a plurality of hooks or such like used to define a predetermined path for a specific tube, wherein each path has a specific defined length. For example, the path defined by the guiding means for the inlet tube may cover a longer distance than the path defined by the guiding means for the outlet tube. In this case, the inlet tube of the fluid bag is longer than the outlet tube of the fluid bag. If the fluid bag is inserted correctly, with the inlet tube running along the path defined by the guiding means for the inlet tube and the outlet tube running along the path defined by the guiding means for the outlet tube, both the inlet tube and the outlet tube project from the guiding means and can be fluidly connected to a haemodialysis machine. However, if the fluid bag is inserted the wrong way, with the inlet tube running along the path defined by the guiding means for the outlet tube and the outlet tube running along the path defined by the guiding means for the inlet tube, the outlet tube is too short to project outward from the relatively long path defined by the guiding means for the inlet tube. Thus, there is no loose end of the outlet tube reachable by the user to fluidly connect the fluid bag to the haemodialysis machine in this position of the fluid bag.

Thus, usage error is reduced due to the user-friendly attachment assembly and if the fluid bag should still be aberrantly inserted in the fluid warmer, the guiding features prevent the aberrantly inserted fluid bag from being fluidly connected to the haemodialysis machine. Thus, patient safety significantly increases.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
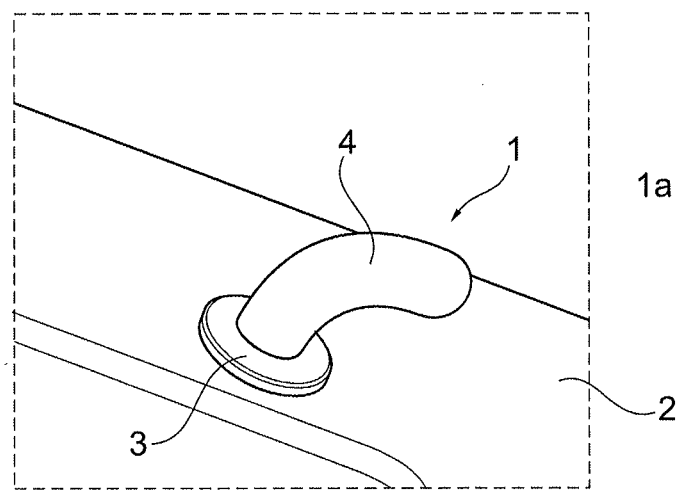
FIG. 1 shows a hook-shaped fixture (FIG. 1a) and a pin-shaped fixture (FIG. 1b)
Figure 1:
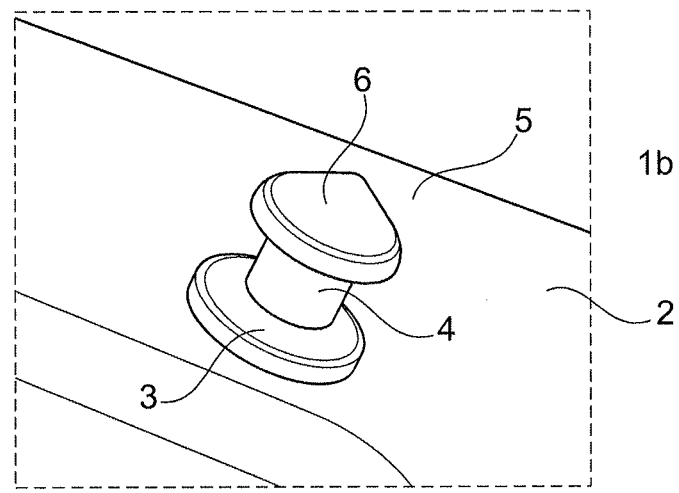

As can be seen from FIG. 1a, a hook-shaped fixture/hook 1 is mounted onto a surface 2 of a fluid warmer 13. The hook 1 comprises a cylindrical shaft 4 bent at an angle relative to the surface 2, and a base 3 providing the necessary structural stability for attaching the hook 1 to the surface 2. The diameter of the base 3 is larger than the diameter of the shaft 4. To ensure easy cleaning of the hook 1, the hook 1 has a smooth outer surface.

FIG. 1b depicts a pin-shaped fixture/pin 5 mounted onto a surface 2 of a fluid warmer. The pin 5 has essentially the shape of an arrow, comprising a cylindrical shaft 4 protruding at right angles to the surface 2 of the fluid warmer 13, and a base 3 providing the necessary structural stability for attaching the pin 5 to the surface 2. The diameter of the base 3 is larger than the diameter of the shaft 4. At the end of the shaft 4 pointing away from the surface 2, an "arrow head" in the form of a conical tip 6 is mounted onto the shaft 4. The base diameter of the conical tip 6 is larger than the diameter of the shaft 4. Thus, the arrow-shaped pin 5 can be inserted into the receiving opening of a fluid bag 7, until the shaft 4 of the at least one pin-shaped fixture 5 projects through the receiving opening. In this position, the increased diameter of the conical tip 6 of the pin 5 lies against the surface of the fluid bag 7 facing away from the fluid warmer 13 and thus prevents the receiving opening of fluid bag 7 from slipping of the pin 5. Hence, the fluid bag 7 is securely locked into position, until a user/nurse removes the fluid bag 7 from the pin 5 again by actively pulling the fluid bag 7.

Figure 2:
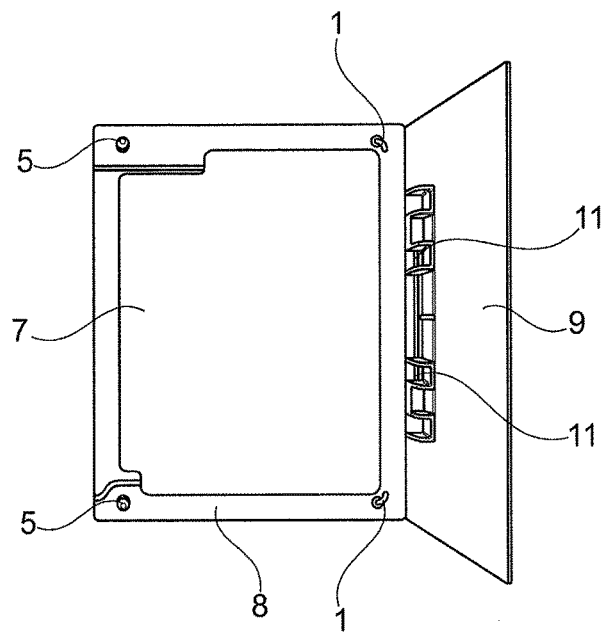
FIG. 2 shows a fluid bag attached to a fluid warmer via an attachment assembly according to aspects of the present invention.

FIG. 2 shows a fluid bag 7 that is fixed to the heat exchange interface on the front housing 8 of a fluid warmer 13. The rear housing part 9 takes the form of a door, that is connect to the front housing part 8 via two hinges 14. In this illustration, the door 9 is in an open position to reveal the fluid bag 7 attached to the front housing 8. Two hooks 1 are mounted on the front housing part 8 immediately adjacent to the area of the heat exchange interface on the side of the area of the heat exchange interface adjacent to the hinges 14. At the side of the area of the heat exchange interface opposite to the hinges 14, two pins 5 are mounted on the front housing part 8. These two pins 5 are aligned with the two hooks 1, to ensure that a fluid bag 7 attached to these hooks 1 and pins 5 is stretched to its full length and lies flat against the heat exchange interface of the front housing part 8 of the fluid warmer 13. While such an alignment of the pins 5 and hooks 1 is advantageous in the present embodiment, the pins 5 and hooks 1 are not necessarily aligned in other embodiments of the present invention.

Figure 3:
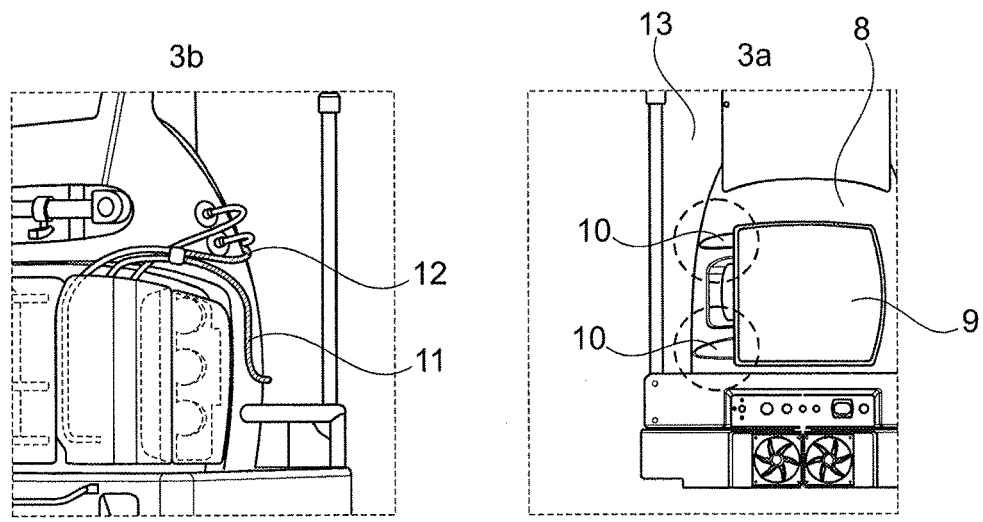
FIG. 3 shows the guiding means of a fluid warmer according to aspects of the present invention (FIG. 3a) as well as the paths defined by the guiding means for the inlet and outlet tubes of a fluid bag (FIG. 3b).

FIG. 3a shows a fluid warmer 13 with tube guiding features 10 in a state in which the door of the rear housing part 9 is closed. The actual heat exchange interface is behind door 9 and can not be seen in this view. These guiding features 10 take the form of recesses or grooves receding into the front housing part 8. When a fluid bag 7 is inserted into the fluid warmer 13 and thus comes to lie between the rear housing part 9 and the front housing part 8, tubes attached to the fluid bag 7 run along the paths 11, 12 defined by the recess of each guiding means 10 and project outward from the fluid warmer 13 to be fluidly connected to e.g., a haemodialysis machine.

As is shown in FIG. 3b, each path 11, 12 defined by a guiding means 10 each has a different length. Thus, each tube running along a different path 11, 12 has to cover a different defined distance before it can project outward from the fluid warmer 13 and can be fluidly connected with a haemodialysis machine. By providing the fluid bag 7 with inlet and outlet tubes that differ from each other in their lengths, it is possible to restrict the possibility of fluidly connecting the fluid bag 7 to cases in which the fluid bag 7 has been correctly inserted into the fluid warmer 13. If for example, the inlet tube is longer than the outlet tube, then the fluid warmer 13 will be configured in such a way, that the inlet tube has to run along the relatively longer defined path 11 in order to reach a connection portion to fluidly connect to a haemodialysis machine. If the fluid bag 7 is correctly inserted, the length of the inlet tube is of a sufficient length to cover the entire distance defined by the path 11. However, if the fluid bag 7 is wrongly inserted and the shorter outlet tube runs along the long path 11 defined by the guiding means 10, the short outlet tube is too short to project from the fluid warmer 13 and reach a connection portion to fluidly connect to a haemodialysis machine. Thus, an operation of the fluid warmer is only possible, if the fluid bag 7 is correctly inserted therein.

The invention claimed is:
1. An attachment assembly comprising:
   a fluid warmer of a system for extracorporeal blood treatment, the fluid warmer comprising:
      a first housing defining a plurality of tube paths;
      at least one first hook-shaped fixture located on the first housing; and
      at least one first pin-shaped fixture located on the first housing spaced from the at least one first hook-shaped fixture by a first predetermined distance;
   a flexible fluid container configured to attach to the fluid warmer, the flexible fluid container comprising:
      at least one first receiving member configured to receive the at least one first hook-shaped fixture; and
      at least one second receiving member configured to receive the at least one first pin-shaped fixture and spaced from the at least one first receiving member by a second predetermined distance in a non-expanded stage of the flexible fluid container, the second predetermined distance being less than the first predetermined distance such that the flexible fluid container will be expanded when the at least one first receiving member is engaged with the at least one first hook-shaped fixture and the at least one second receiving member is engaged with the at least one first pin-shaped fixture; and,
   a plurality of tubes attached to the flexible fluid container, each of the plurality of tubes positioned within a respective one of the plurality of tube paths.

2. The attachment assembly according to claim 1, wherein the at least one first hook-shaped fixture is located and arranged on the fluid warmer such that the flexible fluid container can be hung on the at least one first hook-shaped fixture.

3. The attachment assembly according to claim 2, wherein the at least one first pin-shaped fixture is located and arranged on the fluid warmer such that the flexible fluid container hung on the at least one first hook-shaped fixture is fixed in its position on the fluid warmer using the at least one first pin-shaped fixture when the flexible fluid container is fully expanded or stretched.

4. The attachment assembly according to claim 1, wherein a distance difference between the first and second predetermined distances ensures that the flexible fluid container attached to the at least one first hook-shaped fixture located on the fluid warmer at one end and attached to the at least one first pin-shaped fixture located on the fluid warmer at another end lies flush against the fluid warmer.

5. The attachment assembly according to claim 1, wherein the at least one first hook-shaped fixture and the at least one first pin-shaped fixture are adjacent an interface between the fluid warmer and the flexible fluid container attached to the fluid warmer.

6. The attachment assembly according to claim 1, wherein the at least one first hook-shaped fixture located on the fluid warmer and the at least one first pin-shaped fixture located on the fluid warmer are manufactured of a polymer material or metal.

7. The attachment assembly according to claim 1, wherein the fluid warmer further comprises a rear housing part and a front housing part connected to each other via at least one hinge, the at least one first hook-shaped fixture located a shorter distance from the at least one hinge than the at least one first pin-shaped fixture.

8. The attachment assembly according to claim 1, wherein the at least one first hook-shaped fixture and the at least one first pin-shaped fixture are adjacent an interface between the fluid warmer and the flexible fluid container attached to the fluid warmer.

9. The attachment assembly according to claim 1, wherein each of the plurality of tube paths has a unique defined length.

10. The attachment assembly according to claim 1, wherein lengths of different tubes attached to the flexible fluid container are dimensioned to match lengths of paths defined by guiding means of the fluid warmer.

11. A system for extracorporeal blood treatment comprising the attachment assembly according to claim 1 for attaching the flexible fluid container to the fluid warmer of the system.

* * * * *